United States Patent
Tollin et al.

(10) Patent No.: US 10,155,714 B2
(45) Date of Patent: Dec. 18, 2018

(54) PROCESS FOR THE PURIFICATION OF MONOCHLOROACETIC ACID

(71) Applicant: Akzo Nobel Chemicals International B.V., Arnhem (NL)

(72) Inventors: Lars Magnus Tollin, Skoghall (SE); Melle Rinze Nieuwhof, Dieren (NL); Arie Grootenboer, Arnhem (NL); Jacobus Theodorus Josef Aaldering, Doesburg (NL); Henricus Johannes Marinus Petrus Van Hal, Barneveld (NL); Matheus Theodorus De Groot, Utrecht (NL)

(73) Assignee: AKZO NOBEL CHEMICALS INTERNATIONAL B.V., Arnhem (NL)

( * ) Notice: Subject to any disclaimer, the term of this patent is extended or adjusted under 35 U.S.C. 154(b) by 0 days.

(21) Appl. No.: 15/556,849

(22) PCT Filed: Mar. 14, 2016

(86) PCT No.: PCT/EP2016/055390
§ 371 (c)(1),
(2) Date: Sep. 8, 2017

(87) PCT Pub. No.: WO2016/146556
PCT Pub. Date: Sep. 22, 2016

(65) Prior Publication Data
US 2018/0273462 A1  Sep. 27, 2018

(30) Foreign Application Priority Data
Mar. 17, 2015  (EP) ..................................... 15159373

(51) Int. Cl.
*C07C 51/487* (2006.01)
*C07C 51/377* (2006.01)

(52) U.S. Cl.
CPC .......... *C07C 51/487* (2013.01); *C07C 51/377* (2013.01)

(58) Field of Classification Search
CPC ............................ C07C 51/487; C07C 51/377
(Continued)

(56) References Cited

U.S. PATENT DOCUMENTS 2,863,917 A   12/1958   Rucker et al.
3,739,023 A    6/1973   Sennewald et al.
(Continued)

FOREIGN PATENT DOCUMENTS

CA        1020170 A    11/1977
CN     101528657 A     9/2009
(Continued)

OTHER PUBLICATIONS

Zhu Xiaojun et al., "Current Situation and Research Progress of Dechlorinating Technology", Chemical Production and Technology, 2005, 12(1), pp. 24-28. (English translation of Abstract provided).
(Continued)

*Primary Examiner* — Deborah D Carr
(74) *Attorney, Agent, or Firm* — McDonnell Boehnen Hulbert & Berghoff LLP

(57) ABSTRACT

The present invention pertains to a process for the purification of a feed comprising monochloroacetic acid and dichloroacetic acid wherein the feed is subjected to a catalytic hydrodechlorination step by contacting it with a source of hydrogen to convert dichloroacetic acid into monochloroacetic acid in the presence of a solid heterogeneous hydrogenation catalyst comprising a Group VIII noble metal on a carrier under hydrodechlorination conditions, wherein the reaction is carried out in the presence of a catalyst enhancer which comprises a salt of a metal selected from the group of non-noble metals of Group VIII, Group VIB, Group VIIB,
(Continued)

and Group IIB. It was found that the presence of a catalyst enhancer leads to reduced deactivation of the catalyst and/or increased activity of the spent catalyst. This allows longer production cycles, less downtime, and lower formation of side products. The catalyst enhancer preferably comprises one or more salts of one or more of nickel, cobalt, or iron, more in particular of iron. The salts preferably comprise one or more of chloride salts and acetate salts.

19 Claims, 1 Drawing Sheet

(58) Field of Classification Search
USPC .......................................................... 562/604
See application file for complete search history.

(56) References Cited

U.S. PATENT DOCUMENTS

| | | | |
|---|---|---|---|
| 3,754,029 | A | 8/1973 | Augsburg et al. |
| 4,051,019 | A | 9/1977 | Johnson |
| 4,159,785 | A | 7/1979 | Berry, Jr. |
| 5,191,118 | A | 3/1993 | Correia et al. |
| 5,356,850 | A | 10/1994 | Correia et al. |
| 5,414,116 | A | 5/1995 | Correia |
| 5,449,501 | A | 9/1995 | Luebke et al. |
| 5,758,699 | A | 6/1998 | Haquet et al. |
| 5,962,366 | A | 10/1999 | Zhang |
| 8,101,798 | B2 | 1/2012 | Timmermans et al. |
| 2001/0000035 | A1 | 3/2001 | Ruhl et al. |

FOREIGN PATENT DOCUMENTS

| | | |
|---|---|---|
| CN | 102001930 A | 4/2011 |
| DE | 1 072 980 B | 1/1960 |
| DE | 1 816 931 A1 | 7/1970 |
| DE | 1 915 037 A1 | 10/1970 |
| DE | 43 08 793 A1 | 9/1994 |
| EP | 0 453 690 A1 | 10/1991 |
| EP | 0 557 169 A1 | 8/1993 |
| EP | 0 727 250 A2 | 8/1996 |
| EP | 0 769 462 A1 | 4/1997 |
| FR | 2 647 032 A1 | 11/1990 |
| GB | 1 282 682 A | 7/1972 |
| GB | 1 411 214 A | 10/1975 |
| JP | 62-081350 A | 4/1987 |
| NL | 109769 C | 10/1964 |
| RU | 2 318 796 C1 | 3/2008 |
| RU | 2 391 331 C2 | 6/2010 |
| WO | 99/17877 A1 | 4/1999 |
| WO | 08/025758 A1 | 3/2008 |
| WO | 08/109671 A2 | 9/2008 |
| WO | 09/087994 A1 | 7/2009 |
| WO | 13/057126 A1 | 4/2013 |
| WO | WO-2013057126 A1 * | 4/2013 ........... C07C 51/487 |

OTHER PUBLICATIONS

Chen et al., "Dechlorination of disinfection by-product monochloroacetic acid in drinking water by nanoscale palladized iron bimetallic particle", Journal of Environmental Sciences, 2008, 20(8), 945-951.
English equivalent of: Chen et al., "Dechlorination of monochloroacetic acid with nanoscale Pd/Fe bimetallic particles", Materials Science & Technology, 2009, 17(4), 535-538.
Saroha et al., "Trickle Bed Reactors", Reviews in Chemical Engineering, 1996, 12(3-4), 207-347.
Griffioen et al., "Caring for Catalysts", Hydrocarbon Engineering, 2010, 4 pages.
Bonarowska et al., "Synergistic effects in hydrodechlorination of organic compounds catalyzed by metals", Annales Universitatis Mariae Curie-Sklodowska, Sectio AA: Chemia (2010), 65, LXV(1), 8 pages.
Coq et al., "Bimetallic palladium catalysts: influence of the co-metal on the catalyst performance", Journal of Molecular Catalysis A: Chemical, 2001, 173(1-2), 117-134.
Bodnar et al., "Palladium promoted by metal ions. Oxidation state of promoter during liquid phase hydrogenations", Department Chemical Engineering and Industrial Chemistry, Swiss Federal Institute of Technology, Zurich, 1995, 393-402.

* cited by examiner

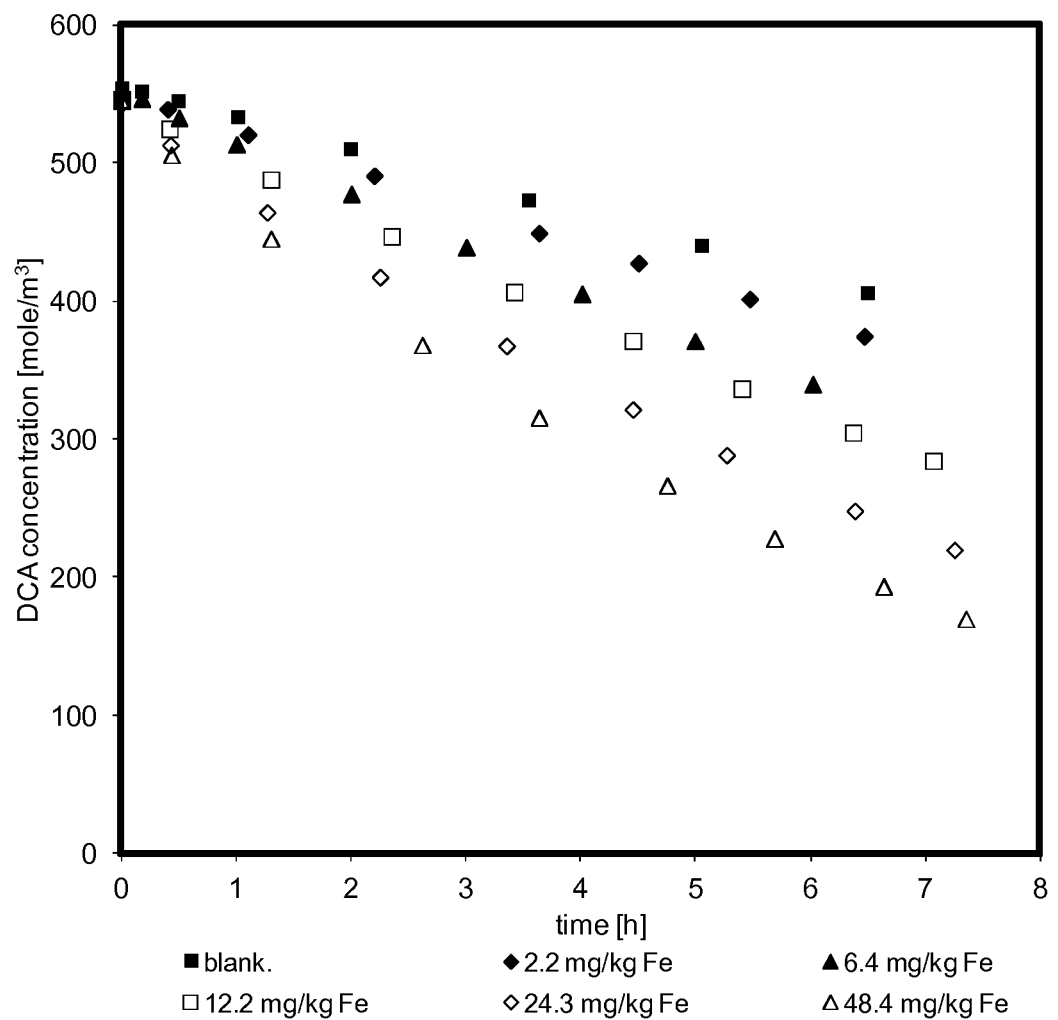

PROCESS FOR THE PURIFICATION OF MONOCHLOROACETIC ACID

This is the US national phase under 35 U.S.C. § 371 of international application PCT/EP2016/055390, filed Mar. 14, 2016, which claims priority to European application EP 15159373.8, filed Mar. 17, 2015.

The present invention relates to a process for the hydrodechlorination of a liquid feed comprising dichloroacetic acid (DCA).

The predominant industrial route for the production of monochloroacetic acid is by reacting acetic acid with chlorine. Such a process is commonly known and generally makes use of a reactor in which a mixture of liquid acetic acid (HAc) is reacted with chlorine under anhydrous conditions, using acetyl chloride as the catalyst. Acetyl chloride is preferably formed in-situ by the addition of e.g. acetic anhydride. In the chlorination reactor, monochloroacetic acid (MCA) and gaseous HCl are formed together with by-products of which dichloroacetic acid (DCA) and trichloroacetic acid (TCA) are examples.

After the MCA-containing reaction product mixture has passed the reactor(s) and the catalyst recovery section, DCA is present in a significant amount, typically about 3-10%. To reduce the amount of DCA in the MCA, the MCA/DCA-containing product mixture is subsequently subjected to a purification process. The purification process can either be a physical separation, such as crystallization or distillation, or a chemical conversion, such as a reduction where DCA is reduced with hydrogen in the presence of a hydrogenation catalyst, e.g. a metal-based catalyst.

As the boiling points of monochloroacetic acid and dichloroacetic acid are very close (189° and 194° C., respectively), removal of DCA from MCA by distillation is expensive and uneconomical.

With crystallization, the concentration of dichloroacetic acid in a crude monochloroacetic acid feed can only be reduced by a factor of approximately 4, i.e., for example, from 3 to 0.7-0.8% by weight, with a one-stage recrystallization. Hence, for the production of pure monochloroacetic acid, the space and time requirements are considerable. Furthermore, after several crystallizations, a mother liquor remains comprising a mixture of monochloroacetic acid and dichloroacetic acid. Although this mother liquor still comprises at least 30% by weight of monochloroacetic acid, depending on the cooling conditions, it cannot be converted into a saleable product by further crystallization and has to be regarded as waste.

It is known that the concentration of dichloroacetic acid in crude monochloroacetic acid can be reduced considerably by a catalytic hydrodechlorination (for example in accordance with U.S. Pat. No. 5,191,118 and U.S. Pat. No. 5,356,850).

This reaction can be carried out in the vapour phase (for example in accordance with NL 109,769 and DE 1,072,980). Alternatively, the hydrodechlorination is carried out in the liquid phase, e.g., in slurry reactors in which the catalyst is finely dispersed in the liquid phase (for example in accordance with U.S. Pat. No. 2,863,917, DE 1,816,931, and WO 2008/025758). Another possibility is to feed the liquid crude monochloroacetic acid to the top of a vertical tubular reactor in which it trickles downwards over a heterogeneous catalyst that is accommodated in a fixed bed, while hydrogen is fed to the top or bottom of the vertical tubular reactor (for example in accordance with U.S. Pat. No. 3,754,029, RU 2,318,796 or RU 2,391,331). These reactors are commonly known as trickle-bed reactors.

WO 2013/057126 describes a process for the hydrochlorination of a liquid feed comprising monochloric acid, dichloroacetic acid, optionally acetic acid and/or trichloroacetic acid. The feed is subjected to a catalytic hydrochlorination step by contacting it with a source of hydrogen in the presence of a solid heterogeneous hydrogenation catalyst situated in a fixed catalyst bed The catalyst that is used in this process generally comprises a Group VIII noble metal on a carrier, in particular palladium. It has been found that the catalyst deactivates rather quickly during use, leading to a decreased conversion. This may be countered by increasing the reaction temperature, but apart from additional energy costs, this also leads to the increased formation of by-products, such as aldehydes that may generate condensation products and other heavy compounds such as glycolic acid monochloroacetate. Further, catalyst deactivation will at some point in time lead to replacement of the catalyst. This causes unit down-time which leads to production loss.

There is therefore need for a process for purification of a feed comprising monochloroacetic acid and dichloroacetic acid through hydrodechlorination using a catalyst comprising a Group VIII noble metal on a carrier, wherein the deactivation of the catalyst is reduced or the activity of the spent catalyst is increased. The present invention provides such a process.

The present invention pertains to a process for the purification of a feed comprising monochloroacetic acid and dichloroacetic acid wherein a feed is subjected to a catalytic hydrodechlorination step by contacting it with a source of hydrogen to convert dichloroacetic acid into monochloroacetic acid in the presence of a solid heterogeneous hydrogenation catalyst comprising a Group VIII noble metal on a carrier under hydrodechlorination conditions, characterized in that the reaction is carried out in the presence of a catalyst enhancer comprising a salt of a metal selected from the group of non-noble metals of Group VIII, Group VIB, Group VIIB, and Group IIB.

BRIEF DESCRIPTION OF THE DRAWINGS

The FIGURE displays dichloroacetic acid concentration in mol/m$^3$ as a function of time for the experiments described in the Examples 1.0-1.5.

It has been found that the presence of a salt of a metal selected from the group of non-noble metals of Group VIII, Group VIB, Group VIIB, and Group IIB leads to an increased activity of (partially) deactivated catalyst and/or a decrease of the catalyst deactivation rate, and thus to longer production cycles, less downtime, and lower formation of side products.

It is noted that GB1282682 describes the activation of noble metal catalysts for selective hydrogenative dehalogenation of dihalocarboxylic acids by adding minor amounts of certain compounds which are not a poison for the noble metal catalyst and are at least partially soluble in the reaction medium. In the examples compounds like the chlorides and acetates of lithium, sodium, potassium, and ammonium are used, as are organic compounds including triethylamine, pyridine, triphenylphosphine, butylacetate, butyraldehyde, and diisobutylketone. This reference indicates that the use of catalyst poisons should be avoided, and explicitly mentions Fe2+, Co2+, and Ni2+ as compounds which are to be avoided. It is therefore particularly surprising that the use of these compounds in fact leads to a decrease in catalyst deactivation rate.

It is further noted that U.S. Pat. No. 5,191,118 describes the addition of sulfur or sulfur compounds during the hydrodechlorination of dichloroacetic acid in monochloroacetic acid. This document does not mention anything about the specific metal salts used in the present invention.

DE4308793 describes a method for manufacturing monochloroacetic acid with a low dichloroacetic acid content wherein the contaminated monochloroacetic acid is subjected to a temperature treatment in the absence of hydrogen in the presence of a non-noble metal, followed by a distillation step. This reference does not describe the hydrodechlorination reaction as effected in the present invention.

WO99/17877 describes a treatment to improve the durability and selectivity of a hydrodechlorination catalyst by the incorporation therein of a halide salt in combination with an alkali metal halide and/or an ammonium halide. The dechlorination catalyst described in this reference is for the carbon tetrachloride.

C. Chao et al. ("Dechlorination of disinfection by-product monochloroacetic acid in drinking water by nanoscale palladized iron bimetallic particle, *Journal of Environmental Sciences* 20 (2008), 945-951) describes the dechlorination in the absence of hydrogen of monochloroacetic acid in a dilute aqueous solution using a catalyst comprising palladium and iron in the context of water purification. This reference does not describe the hydrodechlorination of dichloroacetic acid impurities in monochloroacetic acid.

In one embodiment, in the process according to the invention, the feed is subjected to catalytic hydrodechlorination by contacting it in the liquid phase with a source of hydrogen in the presence of a catalyst and a catalyst enhancer.

In the present invention the reaction is carried out in the presence of a catalyst enhancer comprising a salt of a metal selected from the group of non-noble metals of Group VIII, Group VIB, Group VIIB, and Group IIB of the Periodic Table of Elements (CAS Version as indicated in the *CRC Handbook of Chemistry and Physics*, $88^{th}$ edition, 2007). The salts of metal selected from the group of non-noble metals of Group VIII, Group VIB, Group VIIB, and Group IIB may be indicated as catalyst enhancers in this specification. Obviously combinations of catalyst enhancers may also be used.

Examples of suitable non-noble metals of Group VIII are nickel, cobalt, and iron. These three metals can all exist in the divalent and the trivalent state, and both types are suitable.

Examples of suitable metals of Group VIB are chromium, molybdenum, and tungsten. The use of chromium may be less preferred for reasons of toxicity.

Examples of suitable metals of Group VIIB are manganese, technetium, and rhenium. Of these, manganese is considered preferred.

Examples of suitable metals of Group IIB are zinc and cadmium. The use of cadmium may be less preferred for environmental reasons. Therefore, within this Group the use of zinc is considered preferred.

Overall, the use of a non-noble metal of Group VIII is considered preferred. The use of one or more of nickel, cobalt, and iron is particularly preferred, and the use of salts of iron2+ and/or iron3+ is a preferred embodiment of the present invention.

The enhancer is in the form of a metal salt. While in principle all types of salts may be suitable, it is preferred to use a salt comprising an anion which is already present in the system. Therefore, the use of chloride salts and acetate salts is considered preferred. In general it is preferred to use salts which are soluble in the reaction system, and which are relatively safe from a HSE point of view.

The catalyst enhancer may be provided to the system in the form of its salt. However, due to the circumstances prevailing in the reaction medium it is also possible to provide the enhancer in the form of the metal, as this will lead to the formation of the salt, in particular the acetate and/or chloride, in situ.

The catalyst enhancer may be incorporated into the catalyst in several ways. In one embodiment, the catalyst enhancer is incorporated into the catalyst before use. In another embodiment it is incorporated into the catalyst during use, e.g., through spiking of the feed. In a further embodiment the catalyst enhancer is incorporated into the catalyst after it has been used for a certain period of time, e.g., by providing the catalyst enhancer to the catalyst dissolved in a solvent not under reaction reaction conditions. The several measures may also be combined. It is preferred for at least part of the catalyst enhancer to be provided to the catalyst during use, i.e. under reaction conditions.

The heterogeneous hydrogenation catalyst used according to the present invention preferably comprises between 0.1 and 3% by weight, more preferably between 0.5 and 2% by weight, based on the total weight of the heterogeneous catalyst, of one or more metals of Group VIII of the Periodic Table of the Elements. Preferably, the heterogeneous catalyst comprises ruthenium, rhodium, palladium and/or platinum. More preferably, it comprises palladium, platinum, or a combination thereof. Most preferably, it comprises palladium or Pd and either sulfur or a sulfur compound. For example, the catalysts described in EP0557169 or EP0453690 are suitable for use in the process according to the invention.

The carrier on which the one or more metals of Group VIII of the Periodic Table of the Elements have been deposited is preferably selected from the group consisting of activated carbon, silica, alumina, zirconium oxide, and titanium oxide. Activated carbon is most preferred. The carrier may comprise sulfur or sulfur-containing components (either organic or inorganic in nature).

In one embodiment the catalyst is in the form of a powder, e.g., for slurry processes. In this embodiment, the catalyst preferably is in the form of a powder with a diameter particle size below 800 micrometers (microns), specifically below 500 micrometers (microns). In one embodiment the catalyst has a diameter particle size of at least 5 micrometers (microns), in particular at least 10 micrometers (microns). In one embodiment, the catalyst has a diameter particle size of 50-300 micrometers (microns).

In one embodiment, the catalyst is a particulate catalyst suitable for use in fixed bed operation. In this case, the catalyst may have an average diameter over the entire particle of, e.g., at least 0.8 mm. The particles may be in the form of irregularly shaped granules, spheres, rings, cylinders, trilobes, quadrulobes, or other extrudates. More preferably, said particles are in the form of extrudates, trilobes, or quadrulobes, having a diameter of between 0.8 to 3 mm and a length of between 1 to 10 mm.

The feed used in the process according to the invention comprises monochloroacetic acid and dichloroacetic acid. Optionally, the feed may also comprise trichloroacetic acid. Where trichloroacetic acid is present, it is possible that this compound is also hydrodechlorinated to dichloroacetic acid and/or to monochloroacetic acid under reaction conditions. In one embodiment, the feed comprises between 30 and 99.5% by weight of monochloroacetic acid, in particular between 60 and 99.5% by weight of monochloroacetic acid and between 0.05 and 70% by weight, preferably between 0.05 and 50% by weight, more preferably between 0.05 and 20% by weight, specifically between 1 and 12% by weight, of dichloroacetic acid, and between 0 and 5 wt. % of trichloroacetic acid, in particular between 0 and 2 wt. %.

The process according to the invention is of particular importance for use in the industrial manufacture of monochloroacetic acid. In the context of the present specification industrial manufacture of monochloroacetic acid is meant to refer to the manufacture of monochloroacetic acid in a plant with a capacity of at least 1,000 tonnes of monochloroacetic acid per year and/or a process that uses hydrodechlorination reactors with a volume of at least 0.25 m$^3$.

The process may be carried out in a batch mode or a continuous mode. Where the catalyst is in a fixed bed, as is preferred in the present invention, continuous operation is preferred. Where the catalyst is suspended in the liquid phase, batch mode operation may be preferred.

As it appears that the addition of a catalyst enhancer is particularly attractive for reactivation of catalyst which has been used, the present invention also pertains to a process for the purification of a feed comprising monochloroacetic acid and dichloroacetic acid wherein in a first step the feed is subjected to a catalytic hydrodechlorination step by contacting it with a source of hydrogen in the presence of a solid heterogeneous hydrogenation catalyst comprising a Group VIII noble metal on a carrier under hydrodechlorination conditions, in a second step the catalyst is contacted with a catalyst enhancer comprising a salt of a metal selected from the group of non-noble metals of Group VIII, Group VIB, Group VIIB, and Group IIB to incorporate said salt therein, in a third step the feed is subjected to a catalytic hydrodechlorination step by contacting it with a source of hydrogen in the presence of a solid heterogeneous hydrogenation catalyst comprising a Group VIII noble metal on a carrier under hydrodechlorination conditions and a catalyst enhancer comprising a salt of a metal selected from the group of non-noble metals of Group VIII, Group VIB, Group VIIB, and Group IIB, wherein the second and third steps may be repeated as necessary.

Obviously, the catalyst enhancer may also be present in the first step, if so desired.

In this embodiment, the second step may be carried out under hydrodechlorination conditions, or not. Where the second step is carried out under hydrodechlorination conditions, the present invention pertains to a process for the purification of a feed comprising monochloroacetic acid and dichloroacetic acid wherein the feed is subjected to a catalytic hydrodechlorination step by contacting it with a source of hydrogen to convert dichloroacetic acid into monochloroacetic acid in the presence of a solid heterogeneous hydrogenation catalyst comprising a Group VIII noble metal on a carrier under hydrodechlorination conditions, wherein a catalyst enhancer which comprises a salt of a metal selected from the group of non-noble metals of Group VIII, Group VIB, Group VIIB, and Group IIB is added to the reaction mixture intermittently or continuously.

In one embodiment, the feed used in the process according to the invention preferably comprises
  (i) between 30 and 99.5% by weight of monochloroacetic acid, in particular between 60 and 99.5% by weight of monochloroacetic acid,
  (ii) between 0.05 and 70% by weight, preferably between 0.05 and 50% by weight, more preferably between 0.05 and 20% by weight, specifically between 1 and 12% by weight, of dichloroacetic acid,
  (iii) between 0 and 30% by weight of acetic acid,
  (iv) between 0 and 20% by weight of water, preferably between 0.1 and 10 wt. %, more preferably between 0.1 and 5 wt. %, in particular between 0.1 and 1% by weight of water, most preferably between 0.1 and 0.5% by weight of water, and
  (v) between 0 and 5% by weight of other components, up to a total of 100%, based on the total weight of the liquid feed.

Other components may include a minor amount of acid anhydrides, trichloroacetic acid, bromoacetic acid, and alpha-chloropropionic acid. It is noted that due to the presence of the water, acid chlorides cannot be present in said liquid feed.

In a preferred embodiment of the present invention, the liquid feed is obtained from a section of a monochloroacetic acid production plant in which acetic acid is reacted with chlorine in the presence of a catalyst. The catalyst is preferably acetyl chloride, which may be formed in situ by the addition of acetic anhydride. Residual acetyl chlorides that may still be present in this feed are hydrolyzed by the addition of water. Such a feed typically comprises 3-10 wt. % of dichloroacetic acid.

In another embodiment the liquid feed comprises a much higher percentage of dichloroacetic acid, e.g., a mother liquor from a monochloroacetic acid crystallization stage. The feed may, for example contain at least 30 wt. % of dichloroacetic acid, e.g., 30-70 wt. % of dichloroacetic acid.

The source of hydrogen that is fed to the purification process according to the present invention can be substantially pure hydrogen gas or a gas comprising at least 50 mole % of hydrogen gas and the balance further components which do not interfere with the reaction. Examples of such further components include inert gases such as nitrogen and argon, and hydrochloric acid.

In one embodiment of the process according to the invention, the catalyst enhancer is added to the catalyst before the process starts. However, it has been found to be preferred to add the catalyst enhancer to the liquid feed during the processing, because this allows countering of any leaching of catalyst enhancer from the catalyst.

The addition of catalyst to the liquid feed during processing, which is also indicated as spiking, may be carried out continuously or intermittently. Both embodiments have their advantages. Continuous addition allows for a homogeneous process; intermittent addition allows for tailoring to the observed catalyst deactivation.

When the feed is spiked with the catalyst enhancer, the corresponding metal is present in an amount of say 500 micrograms/kg-10 g/kg. The exact level will depend on the catalyst deactivation observed and on the duration of the spiking. In a preferred embodiment the corresponding metal is present in an amount of 1-5000 mg/kg. In a more preferred embodiment the corresponding metal is present in an amount of 2-2000 mg/kg. In the most preferred embodiment the metal is present in an amount of 5-500 mg/kg.

In the present invention the catalyst enhancer can be added to the process by addition to the feed before or during its provision to the reactor.

The catalyst enhancer may also be added to the reactor as a separate stream. The form in which the catalyst enhancer is provided to the reactor is not critical. It can, e.g., be suitably provided in the form of a solution or dispersion. The use of a solution is preferred.

The process according to the current invention may be performed in a variety of reactor types that are suitable to contact a liquid feed and a source of hydrogen with the solid heterogeneous hydrogenation catalyst comprising one or more metals of Group VIII of the Periodic Table of Elements deposited on a carrier. Examples of such reactors are those in which the catalyst is suspended in the liquid phase, e.g., slurry reactors and those in which the catalyst is situated in a fixed bed. Suitable reaction temperatures may, e.g., range from 100° C. to 200° C., in particular from 145° C. to 175° C. and pressures may e.g. vary from 0.1 MPa to 1.0 MPa, in particular from 0.2 to 1.0 MPa, more preferably from 0.3 to 0.6 MPa. For a fixed bed reactor the values for temperature and pressure refer to the conditions in the top of the reactor.

Suitable slurry reactors are known in the art and comprise, e.g., reactors which are mechanically stirred or stirred via an external slurry recycle that may also drive an ejector (as e.g. mentioned in CN 101528657).

The use of a fixed catalyst bed is preferred. In one embodiment, the liquid feed is provided to the top of a fixed bed reactor, with the hydrogen flow being co-current or countercurrent. In another embodiment the liquid feed is provided to bottom of a fixed bed reactor, with the hydrogen flow being co-current.

In a preferred embodiment a fixed bed is used which is operated in trickle bed mode, meaning that the liquid feed is provided to the top of the reactor and trickles down to the bottom of the reactor. In this embodiment the co-current provision of hydrogen feed is considered preferred.

In one embodiment the hydrodechlorination step is carried out using a vertical tubular reactor containing the solid heterogeneous hydrogenation catalyst as described above in a fixed bed (also sometimes denoted as a stationary bed of catalyst particles). In this embodiment, the liquid feed which is subjected to the catalytic hydrodechlorination process according to the present invention is fed to the top of the vertical tubular reactor. The hydrogen gas or the mixture of hydrogen gas and up to 50 mole % of an inert gas is preferably fed to the top of the vertical tubular reactor (resulting in a co-current downflow with the liquid feed). The hydrogen gas or mixture of hydrogen gas and up to 50 mole % of an inert gas can also be fed from the bottom of the vertical tubular reactor (i.e. countercurrently with the liquid feed); however, as the operating window is smaller (i.e. the capacity of the reactor is limited by flooding), the co-current downflow embodiment is preferred.

As mentioned above, the liquid feed is preferably fed to the top of said vertical tubular reactor, preferably at a superficial mass velocity of between 1 and 10 kg/s per square meter of the horizontal cross-section of said reactor (the term superficial mass velocity (kg/m$^2$/s) refers to the mass flow divided by the horizontal cross-sectional area of said reactor). Preferably, it is fed to the top of said vertical tubular reactor at a superficial mass velocity of at least 2 kg/s per square meter of the horizontal cross-section of said reactor, more preferably at a superficial mass velocity of at least 2.5 kg/s per square meter of the horizontal cross-section of said reactor, and most preferably at a superficial mass velocity of at least 3 kg/s per square meter of the horizontal cross-section of said reactor. Preferably, the liquid feed is fed to the top of said vertical tubular reactor at a superficial mass velocity of at most 8 kg/s per square meter of the horizontal cross-section of said reactor, more preferably at a superficial mass velocity of at most 7 kg/s per square meter of the horizontal cross-section of said reactor, and most preferably at a superficial mass velocity of at most 6 kg/s per square meter of the horizontal cross-section of said reactor.

Preferably, the source of hydrogen is fed to the top or the bottom, preferably to the top, of the vertical tubular reactor at a superficial gas velocity of at least 0.025 Nm$^3$/s per square meter of the horizontal cross-section of the vertical tubular reactor, more preferably at a superficial gas velocity of at least 0.035 Nm$^3$/s per square meter of the horizontal cross-section of the vertical tubular reactor, and most preferably at a superficial gas velocity of at least 0.04 Nm$^3$/s per square meter of the horizontal cross-section of the vertical tubular reactor.

Preferably, it is fed at a superficial gas velocity of at most 0.25 Nm$^3$/s per square meter of the horizontal cross-section of the vertical tubular reactor, more preferably at a superficial gas velocity of at most 0.20 Nm$^3$/s per square meter of the horizontal cross-section of the vertical tubular reactor, and most preferably at a superficial gas velocity of at most 0.15 Nm$^3$/s per square meter of the horizontal cross-section of the vertical tubular reactor.

The temperature in the top of the vertical tubular reactor is preferably kept between 100 and 200° C., and more preferably between 145 and 175° C. The pressure in the top of the vertical tubular reactor is preferably kept between 0.2 and 1.0 MPa, preferably between 0.3 and 0.6 MPa. In one embodiment, the fixed bed reactor has a diameter exceeding 0.4 m.

In order to minimize the risk of liquid maldistribution in the trickle-bed reactor (see e.g. Saroha & Nigam, "Trickle-bed reactors," *Reviews in Chemical Engineering*, 12, 3-4, 207-347, 1996), the fixed bed wherein the heterogeneous hydrogenation catalyst is situated preferably has been prepared by loading the vertical tubular reactor with the heterogeneous hydrogenation catalyst using a dense loading technique. Maldistribution in catalyst beds is known to significantly decrease the reactor's performance and run-time. The dense loading technique is a conventional loading technique where the vertical tubular reactor is loaded with particles of catalyst simultaneously over the entire cross-section of said reactor. The result is that a catalyst bed is obtained which is uniformly loaded and wherein the density is increased when compared to other reactor loading techniques. When compared to sock loading, a well-known loading technique, the density of the catalyst bed has increased by on average at least 10%, as can be found in Gert Griffioen and Michel Wijbrands, "Caring for Catalysts," *Hydrocarbon Engineering*, June 2010. The fixed bed with densely loaded catalyst according to the present invention can for instance be prepared using the well-known Densicat® or the Catapac™ technique. Suitable dense loading methods and equipment are described in EP 769,462, U.S. Pat. No. 4,051,019, U.S. Pat. No. 4,159,785, EP 0727250, WO 2008/109671, and U.S. Pat. No. 5,449,501.

The present invention will be elucidated by the following examples, without being limited thereto or thereby.

General Experimental Procedure

A 1.1 liter tantalized stainless steel Büchi autoclave with a bottom outlet valve and a heating jacket was equipped with a tantalum gas-inducing hollow shaft flat six-blade open turbine impeller and three baffles. The diameter of the impeller was 45 mm and the ratio of the impeller diameter over the diameter of the reactor was 0.54. A cross-shaped basket made from tantalum wire mesh was connected to the stirrer shaft. Further, the reactor was equipped with a glass dip tube to take samples from the reactor and a tantalum tube for the thermocouple to control the reaction temperature. Two gas feed lines were connected to the reactor, one for the introduction of nitrogen and the other one for the introduction of hydrogen to the head space of the reactor. Each gas feed line was equipped with a Brooks mass flow meter. Two tantalum reflux condensers (tap water was used as the cooling medium) were placed in series to cool the gas leaving the reactor and to reflux the condensables to the reactor. The pressure in the reactor was controlled by a back pressure valve that was installed downstream of the two condensers. Downstream of the back pressure valve, the off gases were led through a series of washing bottles (filled with fresh water).

Experiments were done with spent Pd on activated carbon catalyst from a production facility for monochloroacetic acid that was used in a trickle-bed reactor for the hydrodechlorination of dichloroacetic acid. The catalyst was taken from the middle of the catalyst bed and was available in a sufficient amount for all experiments.

The different starting mixtures for the experiments were taken from a large sample (i.e. sufficient for all the experiments) taken from the crude monochloroacetic acid in the hydrogenation feed tank upstream of the hydrogenation section for the hydrodechlorination of dichloroacetic acid in a production facility for monochloroacetic acid. The amount of dichloroacetic acid in this sample was increased to approximately 6% with pure DCA (99+%) from Acros.

Anhydrous iron(II)chloride (10 mesh; 99.99%) from Aldrich (Product no. 450936) was added to the reaction mixture as a solution in acetic acid (10 grams of anhydrous Fe(II)chloride per liter of acetic acid).

An experiment is started when spent catalyst is loaded in the tantalum basket. Then the reactor is flushed with nitrogen at ambient temperature and pressure to remove oxygen. Subsequently, the nitrogen feed is shut off and hydrogen is fed overnight at a rate of 1.8 Nl/h (Nl is the gas volume at 1 atm and 0° C.) at ambient temperature and pressure. The reactor is heated the next day to a temperature of 80° C. The reaction mixture is added to the reactor when this temperature has been reached. Subsequently, the temperature of the reaction mixture is increased to 150° C., while slowly stirring. When this temperature is reached, the hydrogen flow is increased to 46 Nl/h, the pressure is adjusted to 2.5 bar and the stirrer speed is increased to 1,000 rpm. Samples are taken from the reaction mixture to analyze the change of the dichloroacetic acid concentration with time.

EXAMPLE 1.0—COMPARATIVE

The tantalum basket was filled with 12.02 grams of catalyst and the reactor was filled with 725 grams of the starting mixture, and operated as described above. Iron chloride was not added.

EXAMPLE 1.1

The tantalum basket was filled with 13.37 grams of catalyst and the reactor was filled with 716 grams of the starting mixture, and operated as described above. Iron(II) chloride was added in solution to an amount of 4.9 mg $FeCl_2$ per kg starting mixture (2.2 mg/kg Fe).

EXAMPLE 1.2

The tantalum basket was filled with 14.27 grams of catalyst and the reactor was filled with 723 grams of the starting mixture, and operated as described above. Iron(II) chloride was added in solution to an amount of 14.5 mg $FeCl_2$ per kg starting mixture (6.4 mg/kg Fe).

EXAMPLE 1.3

The tantalum basket was filled with 13.97 grams of catalyst and the reactor was filled with 724 grams of the starting mixture and operated as described above. Iron(II) chloride was added in solution to an amount of 27.7 mg $FeCl_2$ per kg starting mixture (12.2 mg/kg Fe).

EXAMPLE 1.4

The tantalum basket was filled with 14.00 grams of catalyst and the reactor was filled with 729 grams of the starting mixture and operated as described above. Iron(II) chloride was added in solution to an amount of 55.2 mg $FeCl_2$ per kg starting mixture (24.3 mg/kg Fe).

EXAMPLE 1.5

The tantalum basket was filled with 14.00 grams of catalyst and the reactor was filled with 735 grams of the starting mixture and operated as described above. Iron(II) chloride was added to an amount of 110 mg $FeCl_2$ per kg starting mixture (48.4 mg/kg Fe).

Results

The DCA concentration in mole/m$^3$ for the various experiments is presented in FIG. 1. As can be seen from the FIGURE, the addition of iron(II)chloride leads to an improved DCA conversion, as can be seen from a decreased DCA concentration. When more iron(II)chloride is added, the DCA conversion is further improved.

The invention claimed is:

1. A process for the purification of a feed comprising monochloroacetic acid and dichloroacetic acid wherein the feed is subjected to a catalytic hydrodechlorination step by contacting it with a source of hydrogen to convert dichloroacetic acid into monochloroacetic acid in the presence of a solid heterogeneous hydrogenation catalyst comprising a Group VIII noble metal on a carrier under hydrodechlorination conditions, wherein the reaction is carried out in the presence of a catalyst enhancer which comprises a salt of a metal selected from the group of non-noble metals of Group VIII, Group VIB, Group VIIB, and Group IIB.

2. The process according to claim 1 wherein the heterogeneous catalyst comprises between 0.1 and 3% by weight, based on the total weight of the heterogeneous catalyst, of one or more noble metals of Group VIII of the Periodic Table of the Elements.

3. The process according to claim 1 wherein the carrier is selected from the group consisting of activated carbon, silica, alumina, zirconium oxide, and titanium oxide, and optionally comprises sulfur or one or more sulfur-containing components.

4. The process according to claim 1 wherein the heterogeneous catalyst comprises palladium and/or platinum as noble metals of Group VIII of the Periodic Table of the Elements.

5. The process according to claim 1 wherein the catalyst enhancer comprises one or more salts of one or more of nickel, cobalt, iron, molybdenum, tungsten, manganese, or zinc.

6. The process according to claim 1 wherein the salt comprises one or more of chloride salts and acetate salts.

7. The process according to claim 1 wherein the catalyst enhancer is provided to the process through addition to the feed during reaction.

8. The process according to claim 1 wherein the catalyst enhancer is provided to the process through addition to the catalyst not under reaction conditions.

9. The process according to claim 1 wherein
in a first step the feed is subjected to a catalytic hydrodechlorination step by contacting it with a source of hydrogen in the presence of a solid heterogeneous hydrogenation catalyst comprising a Group VIII noble metal on a carrier under hydrodechlorination conditions, in a second step the catalyst is contacted with a catalyst enhancer comprising a salt of a metal selected from the group of non-noble metals of Group VIII, Group VIB, Group VIIB, and Group IIB to incorporate said salt therein, in a third step the feed is subjected to a catalytic hydrodechlorination step by contacting it with a source of hydrogen in the presence of a solid heterogeneous hydrogenation catalyst comprising a Group VIII noble metal on a carrier under hydrodechlorination conditions and a catalyst enhancer comprising a salt of a metal selected from the group of non-noble metals of Group VIII, Group VIB, Group VIIB, and Group IIB, wherein the second and third steps may be repeated as necessary.

10. The process according to claim 9 wherein a catalyst enhancer is also present in the first step.

11. The process according to claim 9, wherein a catalyst enhancer is not present in the first step.

12. The process according to claim 1 wherein the catalyst is suspended in the liquid feed.

13. The process according to claim 1 wherein a liquid feed comprising monochloroacetic acid and dichloroacetic acid is subjected to a catalytic hydrodechlorination step by contacting it with a source of hydrogen to convert the dichloroacetic acid into monochloroacetic acid in the presence of a solid heterogeneous hydrogenation catalyst comprising one or more metals of Group VIII of the Periodic Table of the Elements deposited on a carrier, said catalytic hydrodechlorination step being carried out in a vertical tubular reactor, with the solid heterogeneous hydrogenation catalyst being situated in a fixed catalyst bed, wherein the liquid feed is fed to the top of said vertical tubular reactor at a superficial mass velocity of between 1 and 10 kg/s per square meter of the horizontal cross-section of the vertical tubular reactor and a rate of between 250 and 3,000 kg/hr per $m^3$ of said catalyst bed, wherein the source of hydrogen is fed to the top or bottom of the vertical tubular reactor at a superficial gas velocity of between 0.025 to 0.25 Nm3/s per square meter of the horizontal cross-section of the vertical tubular reactor, so as to obtain an average axial pressure gradient of at least 2 kPa per meter of said catalyst bed, and wherein the temperature in the top of the vertical tubular reactor is between 100 and 200° C., and wherein the pressure in the top of the vertical tubular reactor is between 0.2 and 1.0 MPa.

14. The process according to claim 13 wherein the superficial mass velocity is between 2.5 and 6 kg/s per square meter of the horizontal cross-section of the vertical tubular reactor.

15. The process according to claim 1 wherein the feed comprises
- between 30 and 99.5% by weight of monochloroacetic acid, in particular between 60 and 99.5% by weight of monochloroacetic acid,
- between 0.05 and 70% by weight of dichloroacetic acid,
- between 0 and 30% by weight of acetic acid,
- between 0 and 20% by weight of water, and
- between 0 and 5% by weight of other components, up to a total of 100%, based on the total weight of the liquid feed.

16. The process according to claim 2, wherein the heterogeneous catalyst comprises between 0.5 and 2% by weight based on the total weight of the heterogeneous catalyst, of one or more noble metals of Group VIII of the Periodic Table of the Elements.

17. The process according to claim 5 wherein the catalyst enhancer is iron.

18. The process according to claim 15, wherein the feed comprises between 1 and 12% by weight of dichloroacetic acid.

19. The process according to claim 15, wherein the feed comprises between 0.1 and 0.5% by weight of water.

* * * * *